(12) United States Patent
Anderson

(10) Patent No.: US 10,130,286 B2
(45) Date of Patent: Nov. 20, 2018

(54) PRESSURE-SENSING DEVICE WITH BIPLANAR SENSOR ARRAY

(71) Applicant: MedicusTeK Inc., Taipei (TW)

(72) Inventor: Mark Anderson, Taipei (TW)

(73) Assignee: MedicusTek Inc., Taipei (TW)

( * ) Notice: Subject to any disclaimer, the term of this patent is extended or adjusted under 35 U.S.C. 154(b) by 907 days.

(21) Appl. No.: 13/651,202

(22) Filed: Oct. 12, 2012

(65) Prior Publication Data

US 2014/0107532 A1   Apr. 17, 2014

(51) Int. Cl.
*A61B 5/11* (2006.01)
*A61B 5/00* (2006.01)
*G01L 1/20* (2006.01)

(52) U.S. Cl.
CPC .......... *A61B 5/1122* (2013.01); *A61B 5/6892* (2013.01); *G01L 1/205* (2013.01); *A61B 2562/0247* (2013.01); *A61B 2562/046* (2013.01); *A61B 2562/164* (2013.01)

(58) Field of Classification Search
CPC ........... G01L 1/20–1/205; G01L 1/146–1/148; A61B 2562/0247; A61B 2562/046; A61B 2562/164
See application file for complete search history.

(56) References Cited

U.S. PATENT DOCUMENTS

| | | | |
|---|---|---|---|
| 5,431,064 A * | 7/1995 | Franz | 73/862.68 |
| 5,760,530 A * | 6/1998 | Kolesar | H01L 27/20 310/317 |
| 7,090,647 B2 | 8/2006 | Mimura et al. | 600/587 |
| 7,278,326 B2 | 10/2007 | Kobayashi et al. | 73/862.041 |
| 2005/0110768 A1 | 5/2005 | Marriott et al. | 345/173 |
| 2005/0145045 A1* | 7/2005 | Papakostas et al. | 73/864 |
| 2008/0150906 A1* | 6/2008 | Grivna | G06F 3/0416 345/173 |
| 2009/0070939 A1 | 3/2009 | Hann | 5/652.1 |
| 2012/0022799 A1 | 1/2012 | Ikebe | 702/41 |
| 2012/0283979 A1 | 11/2012 | Bruekers et al. | 702/104 |

(Continued)

FOREIGN PATENT DOCUMENTS

| | | | | |
|---|---|---|---|---|
| CN | 1643358 | 7/2005 | | G01L 1/14 |
| CN | 1655718 | 8/2005 | | A61B 5/11 |

(Continued)

*Primary Examiner* — Rene Towa
*Assistant Examiner* — H. Q. Nguyen
(74) *Attorney, Agent, or Firm* — Osha Liang LLP

(57) ABSTRACT

A pressure-sensing device is disclosed, which includes a pressure sensor pad. The pressure sensor pad includes a first planar substrate, a second planar substrate, first signal lines, second signal lines, a plurality of rows of first sensor components, and a plurality of columns of second sensor components. The first signal lines and the rows of first sensor components are formed on the first planar substrate, and each row of the first sensor components is connected to a corresponding one of the first signal lines. The second planar substrate is disposed opposite to the first planar substrate. The second signal lines and the columns of second sensor components are formed on the second planar substrate, and each column of the second sensor components is connected to a corresponding one of the second signal lines, where the second sensor components face the first sensor components respectively.

20 Claims, 18 Drawing Sheets

(56) References Cited

U.S. PATENT DOCUMENTS

2013/0098162 A1* 4/2013 Chiou et al. .................... 73/753
2013/0207911 A1* 8/2013 Barton .................. G06F 3/0488
                                                          345/173

FOREIGN PATENT DOCUMENTS

| CN | 100353373 | 12/2007 | ............. G06F 3/033 |
| CN | 102346546 | 2/2012 | ............... G06F 3/01 |
| CN | 102665548 | 9/2012 | ............... A61B 5/11 |
| TW | 200517928 | 6/2005 | ............... G06F 3/03 |

* cited by examiner

PRESSURE-SENSING DEVICE WITH BIPLANAR SENSOR ARRAY

BACKGROUND

Technical Field

The present disclosure relates to electronic devices, and more particularly, pressure-sensing devices.

Description of Related Art

There are a number of existing methods and apparatuses that are capable of providing for real-time monitoring of a patient's vital statistics ("vitals"). These apparatuses include electrocardiogram recorders, heart rate monitors, blood pressure monitors, electroencephalographs, pulse monitors, oximeters, carbon dioxide meters, thermostats, scales, maternal uterine activity monitors, and various other non-invasive medical instruments.

However, there is an urgent need for advances in medical instrumentation that monitors patient position and motion in bed. Such monitoring can enable the early warning of health professionals when a patient experiences a seizure or when a patient at risk of falling attempts to exit the bed. Analysis of changes in patient position and movement behavior over time can provide insight into underlying health and responses to medication. These changes are indicative of sleep patterns, activity levels, body repositioning in response to perceived pain, and susceptibility to decubitus ulcers (pressure sores) due to lack of movement. Understanding this "body language" is especially relevant when caring for patients who have difficulty communicating with health professionals and caregivers.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a pressure-sensing device that can be used for monitoring a patient.

According to one embodiment of the present invention, a pressure-sensing device includes a pressure sensor pad. The pressure is sensor pad includes a first planar substrate, a second planar substrate, first signal lines, second signal lines, a plurality of rows of first sensor components, and a plurality of columns of second sensor components. The first signal lines and the rows of first sensor components are formed on the first planar substrate, and each row of the first sensor components is connected to a corresponding one of the first signal lines. The second planar substrate is disposed opposite to the first planar substrate. The second signal lines and the columns of second sensor components are formed on the second planar substrate, and each column of the second sensor components is connected to a corresponding one of the second signal lines, where the second sensor components face the first sensor components respectively, and any one of the first sensor components and a corresponding one of the second sensor components construct a pressure sensor.

Each of the first and second sensor components is a hexagonal sensor component.

Each of the first sensor components includes a first conductive loop and a plurality of first conductive lines. The first conductive loop is formed on the first planar substrate. The first conductive lines are disposed within and connected to the first conductive loop, and arranged in a first direction.

In addition, each of the second sensor components includes a second conductive loop and a plurality of second conductive lines. The second conductive loop is formed on the second planar substrate. The second conductive lines are disposed within and connected to the second conductive loop, and arranged in a second direction.

The first sensor components consist of conductive material printed on the first planar substrate, and the second sensor components consist of conductive material printed on the second planar substrate.

The pressure sensor pad may include a plurality of spacers. The spacers are disposed between the first planar substrate and the second planar substrate.

The spacers can be divided into first spacers fastened on the first planar substrate and second spacers fastened on the second planar substrate, and the first spacers and the second spacers can be coupled together, so as to prevent the first and second sensor components from misalignment.

The first planar substrate or the second planar substrate is flexible for allowing contact between the first and second planar substrates when a sufficient force is applied to the first or second planar substrates.

The first and second sensor components are about the same size.

Each of the first and second sensor components has about the same shape.

Each of the first and second sensor components has a convex shape.

The first sensor components are formed on only one side of the first planar substrate, and the second sensor components are formed on only one side of the second planar substrate.

The first signal lines are select lines, and the second signal lines are read lines; alternatively, the first signal lines are read lines, and the second signal lines are select lines.

The pressure-sensing device may further include a scanning unit and a measuring unit. The scanning unit can periodically scan the select lines one by one. The measuring unit can measure resulting signals on the read lines.

The pressure-sensing device may further include a processing unit. The processing unit can detect a pressure state of each of the pressure sensors based on the resulting electric signals.

When any one of the resulting electric signals is relatively low, the pressure state of a corresponding one of the pressure sensors is an OFF state; when any one of the resulting electric signals is relatively high, the pressure state of a corresponding one of the pressure sensors is an ON state.

When a patient lies on the pressure sensor pad, the processing unit calculates variations of the resulting electric signals to analyze the body position and motion of the patient.

A connection between the processing unit and the scanning unit is wireless, and a connection between the processing unit and the measuring unit is wireless.

According to another embodiment of the present invention, a pressure-sensing device includes a pressure sensor pad. The pressure sensor pad includes a first planar substrate, a second planar substrate, first signal lines, second signal lines, third signal lines, fourth signal lines, a first matrix array of sensor components, and a second matrix array of sensor components. The first signal lines are formed on the first planar substrate. The second signal lines are formed on the first planar substrate and are disconnected from the first signal lines. The first matrix array of sensor components is formed on the first planar substrate, where the first matrix array of sensor components is divided into a plurality of rows of first sensor components connected to the first signal lines and a plurality of columns of second sensor components connected to the second signal lines. The second planar substrate is disposed opposite to the first planar substrate. The third signal lines are formed on the second planar substrate. The fourth signal lines are formed on the second planar substrate and are disconnected from the third signal lines. The second matrix array of sensor components is formed on the second planar substrate, where the second matrix array of sensor components is divided into a plurality of rows of third sensor components connected to the third signal lines and a plurality of columns of fourth sensor components connected to the fourth signal lines. The second matrix array of sensor components faces the first matrix array of sensor components respectively, any one of the first sensor components and a corresponding one of the fourth sensor components construct a pressure sensor, any of the second sensor components and a corresponding one of the third sensor components construct a pressure sensor, and an arrangement of the first signal lines, the second signal lines and the first matrix array is equal to an arrangement of the third signal lines, the fourth signal lines and the second matrix array.

Each of the sensor components is a hexagonal sensor component.

Each sensor component of the first matrix array includes a first conductive loop and a plurality of first conductive lines. The first conductive loop is formed on the first planar substrate. The first conductive lines are disposed within and connected to the first conductive loop, and arranged in a first direction.

In addition, each sensor component of the second matrix array includes a second conductive loop and a plurality of second conductive lines. The second conductive loop is formed on the second planar substrate. The second conductive lines are disposed within and connected to the second conductive loop, and arranged in a second direction.

The first matrix array of sensor components consists of conductive material printed on the first planar substrate, and the second matrix array of sensor components consists of conductive material printed on the second planar substrate.

The pressure sensor pad may include a plurality of spacers. The spacers are disposed between the first planar substrate and the second planar substrate.

The spacers can be divided into first spacers fastened on the first planar substrate and second spacers fastened on the second planar substrate, and the first spacers and the second spacers can be coupled together, so as to prevent the first and second sensor components from misalignment.

The first planar substrate or the second planar substrate is flexible for allowing contact between the first and second planar substrates when a sufficient force is applied to the first or second planar substrates.

The sensor components are about the same size.

Each of the sensor components has about the same shape.

Each of the sensor components has a convex shape.

The first sensor components are formed on only one side of the first planar substrate, and the second sensor components are formed on only one side of the second planar substrate.

The first and third signal lines are select lines, and the second and fourth signal lines are read lines; alternatively, the first and third signal lines are read lines, and the second and fourth signal lines are select lines.

The pressure-sensing device may further include a scanning unit and a measuring unit. The scanning unit can periodically scan the select lines one by one. The measuring unit can measure resulting electric signals on the read lines and select lines.

The pressure-sensing device may further include a processing unit. The processing unit can detect a pressure state of each of the pressure sensors based on the resulting electric signals.

When any one of the resulting electric signals is relatively low, the pressure state of a corresponding one of the pressure sensors is an OFF state; when any one of the resulting electric signals is relatively high, the pressure state of a corresponding one of the pressure sensors is an ON state.

When a patient lies on the pressure sensor pad, the processing unit calculates variations of the resulting electric signals to analyze the body position and motion of the patient.

A connection between the processing unit and the scanning unit is wireless, and a connection between the processing unit and the measuring unit is wireless.

Many of the attendant features will be more readily appreciated, as the same becomes better understood by reference to the following detailed description considered in connection with the accompanying drawings.

BRIEF DESCRIPTION OF THE DRAWINGS

The present description will be better understood from the following detailed description read in light of the accompanying drawing, wherein.

DETAILED DESCRIPTION

Figure 1:
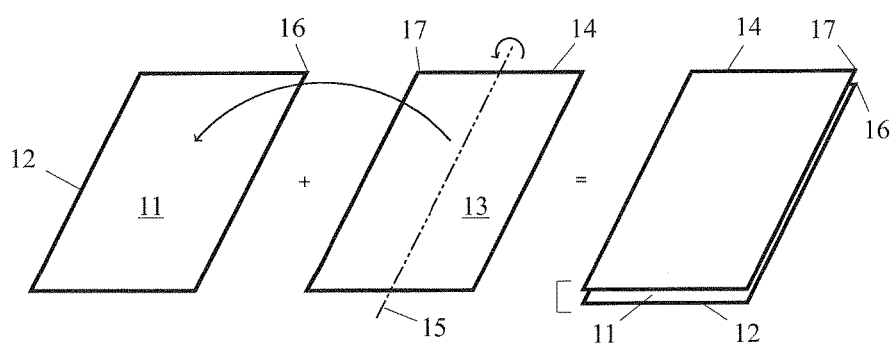
FIG. 1: Illustration of the process whereby two planar substrates are combined to create a sensor array according to one embodiment of the present disclosure.

In the following detailed description, for purposes of explanation, numerous specific details are set forth in order to attain a thorough understanding of the disclosed embodiments. It will be apparent, however, that one or more embodiments may be practiced without these specific details. In other instances, well-known structures and devices are schematically shown in order to simplify the drawing.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure discloses two designs for a pressure pressure-sensing device with a biplanar sensor array. It describes features that include, but are not limited to, sensor shape, an overall arrangement of a plurality of sensors within an array, an arrangement of a plurality of connecting lines between sensors, and a mechanism for measuring sensor states using a plurality of signal lines. Of particular relevance are geometrical attributes of both the sensor shape and the arrangement of sensors within an array that together allow for effective measurement of position and motion of an object on, or above, a sensor array.

Biplanar Design for the Sensor Array

The pressure-sensing device includes a pressure sensor pad that contains a biplanar array of pressure sensors. The biplanar array of pressure sensors comprises sensor components, signal lines, and connecting lines disposed on two planar substrates. Two design features are the sensor shape and the arrangement, or positioning, of a collection, or set, of sensors on the planar substrates. In one embodiment, the geometrical arrangements considered are variations of rectangular grids, or arrays. In this embodiment, indexing, or enumerating, the sensors in the collection using an ordered pair of indices, or subscripts, is natural. Thus, the inventor works with an m×n array of sensors $S_{i,j}$ where $1 \leq i \leq m$ and $1 \leq j \leq n$. The array, or matrix, of sensors is arranged in an approximately grid-like pattern containing m rows and n columns. The sensor array is constructed using a first planar substrate (first plane) $P_1$ and a second planar substrate (second plane) $P_2$. In one embodiment, the planar substrates are manufactured using thin-rolled polyethylene terephthalate (PET). Alternatively, in another embodiment, the planar substrates may be manufactured using polypropylene fabric or polyethylene sheet material, but the present invention is not limited thereto. The planar substrates contain sensor components distributed in the following manner.

- Each sensor $S_{i,j}$ is formed from two sensor components $A_{i,j}$ and $B_{i,j}$.
- For any index pair (i, j), the sensor components $A_{i,j}$ and $B_{i,j}$ are positioned on distinct, or different, planar substrates.
- The sensor components are positioned so that $P_2$ can be superimposed, or overlaid, on $P_1$ in such a way that for each index pair (i, j), sensor components $A_{i,j}$ and $B_{i,j}$ meet, or overlap.

In one embodiment, additional materials to construct sensor components, connecting lines, and signal lines are affixed to one side, or face, of each planar substrate. Alternatively, in another embodiment, these additional materials may be affixed to both sides of a planar substrate, which offers an advantage of providing more available surface area for electrically conductive connecting lines and signal lines. Nevertheless, applying additional materials to only one side of a planar substrate may result in a lower manufacturing cost and provide protection to sensor components, connecting lines, and signal lines. During assembly the two planar substrates are combined, or joined, so that sides containing these additional materials face one another. That is, the additional materials are sandwiched between the two planar substrates forming one complete sensor array. When a durable substance, such as thin-rolled polyethylene terephthalate (PET), is selected to manufacture the planar substrates, they may provide impact resistance and effective moisture barriers. Thus, the biplanar design can provide protection against impact damage and corrosion for the additional sensor components, connecting lines, and signal lines. FIG. 1 shows the process of combining two planar substrates. Additional materials to construct sensor components, connecting lines, and signal lines are affixed to face 11 of first planar substrate 12 and to face 13 of is second planar substrate 14. These additional materials are not included in the figure so as to focus attention on the process of combining the two planar substrates. Second planar substrate 14 is rotated about a central axis 15 and translated to rest on first planar substrate 12 aligning corners 16 and 17.

Binary Detectors

In one embodiment, each pressure sensor can indicate only two states; that is, it is a "binary detector". It measures, or detects, the presence of an object on, or above, the sensor without an ability to more precisely distinguish the location of the object above the interior of the sensor relative to the sensor edges. It can not determine the magnitude of the force or pressure exerted by the object on the sensor, and it can not distinguish multiple objects on the sensor. The sensor simply indicates that either AN OBJECT IS PRESENT or that NO OBJECT IS PRESENT on the sensor. Alternatively, in another embodiment, each pressure sensor can indicate multiple states. A disadvantage of using a binary detector is that it provides less information than, for example, a piezoelectric sensor, which, in an appropriate electric circuit, provides an electrical signal that varies with the magnitude of an applied pressure. Nevertheless, an advantage of using binary detectors is that binary detectors can be manufactured at lower cost than detectors that indicate more than two states and thereby provide more information. This makes the use of binary detectors economically viable in more widespread settings and applications.

Sensitivity and Sensor Size

In one embodiment, each sensor is about the same size. If each sensor is a binary detector, indicating that either AN OBJECT IS PRESENT or that NO OBJECT IS PRESENT on, or above, the sensor, then a sensor array in which all sensors are approximately the same size provides more uniform precision of position measurements when determining the position of an object on the array. If an array of sensors that are binary detectors is used to determine the location of an observed object and the sensors are different sizes, then the array will determine location with different precisions at different positions on the array. In particular, a small sensor will determine the location of the object with greater precision than a large sensor. To avoid this problem when constructing an array of sensors that are binary detectors, it is advantageous to use sensors that are the same size, or nearly so, consistent with reasonably available manufacturing processes. In another embodiment, the sensors may be different sizes. While using sensors of different sizes causes variation in measurement precision across an array of binary detectors, this offers some advantage by widening the range of design possibilities for the sensor array.

Distance Distortion and Convexity

Figure 2:
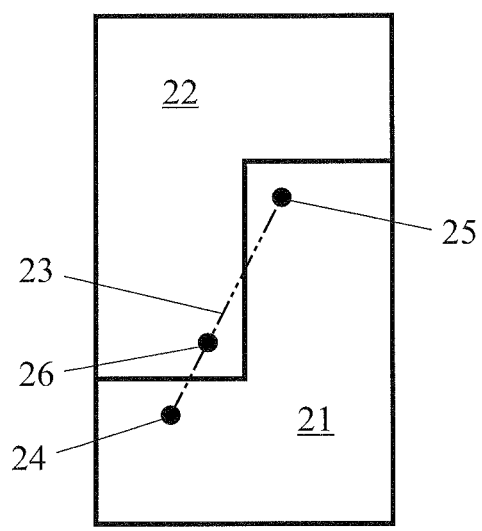
FIG. 2: Illustration of distance distortion using a top view of two adjacent sensors according to an embodiment including sensors that do not have convex shape.

In one embodiment, each sensor has a convex shape. Alternatively, in another embodiment, sensors may a have non-convex shape such as a star shape or "L" shape as illustrated in FIG. 2. The inventor finds that the convex shape is advantageous because it reduces distance distortion that can negatively impact the quality of information about changes in an object's position derived from measuring the object's position at different times using a pressure-sensing device. This is particularly useful when monitoring the motion of an object on, or above, the sensor array. Distance distortion occurs if the sensors are not convex in shape. In general, a shape is convex if for any two locations, or points, in the shape, all locations on the straight line segment between these two locations are also in the shape. FIG. 2 illustrates an example that indicates why this is a design criterion for the shape of a sensor that is a binary detector, which simply indicates whether AN OBJECT IS PRESENT or NO OBJECT IS PRESENT on, or above, the sensor. FIG. 2 presents a top view of two non-convex sensors 21 and 22 that are binary detectors, which are considered, for this example, to be two sensors in an array of sensors that is part of a sensing array used to measure motion. Internal sensor features and additional sensors in the array are not included in the drawing to focus attention on the shapes of these two adjacent sensors. Since some locations on the straight line segment 23 between location 24 and location 25 in sensor 21 are not located, or do not lie, in sensor 21, the shape of sensor 21 is not convex. Suppose that the pressure-sensing device records, or measures, that the object is over sensor 21 when the object is at location 24. If the object moves along the line segment so that at the next recording opportunity the object is at location 25, then the pressure-sensing device records that the object is still over sensor 21. This is the same measurement that would result if the object were stationary at location 24. In contrast, if the object moves a shorter distance along the line segment from location 24 so that at the next recording opportunity the object is at location 26, then the sensor device records that the object has moved from a position over sensor 21 to a position over sensor 22.

Figure 3:
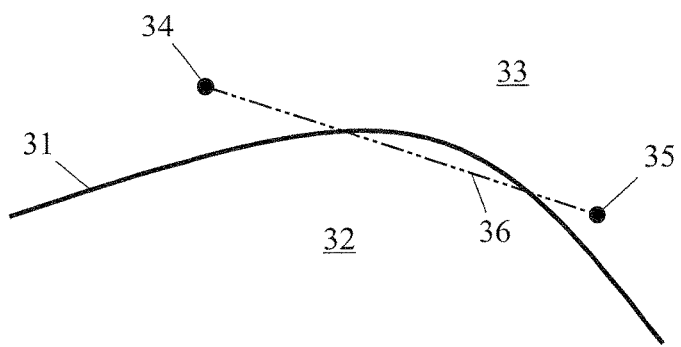
FIG. 3: Illustration of the fact that if neighboring, or adjacent, sensors that share an edge both have convex shape, then the common edge is a straight line segment.

The use of sensors having convex shapes influences design decisions regarding the contours of the perimeters, or boundary edges, of the sensors. To enable the manufacture of densely packed, or tightly arranged, sensor components on the planar substrate, the contours of the sensor edges are selected to be consistent with those in geometrical tilings, or tessellations, of the plane where the tiles completely cover the ideal plane and share edges, but do not overlap. Because the sensor edges are designed this way, as production technologies improve and sensors can be manufactured nearer together, the fraction of planar substrate covered with sensors can be increased more effectively. Consider the case of two adjacent sensors actually touching, or sharing edges. FIG. 3 shows a portion of edge 31 that is shared between sensor 32 and the adjacent, or neighboring, sensor 33. If edge 31 is not a straight line segment, then it is possible to find two locations, or points, location 34 and location 35 in sensor 33 that are sufficiently close to the edge that the line segment 36 between them crosses edge 31. Since not all points on line segment 36 lie in sensor 33, the shape of sensor 33 is not convex. Thus, to create a sensor array design that reduces distance distortion and facilitates dense packing of sensors on the planar substrate, sensors have a convex shape with straight edges.

Directional Bias and Sensor Shape

In one embodiment, the sensors all have about the same shape. Alternatively, in another embodiment, the sensors may have different shapes. While allowing different shapes increases the range of design possibilities for a sensor array, the inventor finds that uniformity is advantageous because it reduces directional bias when measuring the movement of an object on, or above, the sensor array. Directional bias arises when the sensor array provides more precise information about motion in one direction from a particular location than it does about motion in a different direction from that location. Algorithms implemented in a processing unit of a pressure-sensing device may compensate for directional bias, but this may utilize information about the sensor shape encoded within the algorithms or provided to the algorithms as input parameters. That is, algorithms are matched to the shape of sensors in the sensor array. As a practical matter, it would be more difficult, or less effective, to use the sensor array produced by one manufacturer with a processing unit produced by, or algorithms written by, a different manufacturer for an array of sensors of having a different shape.

Figure 4:
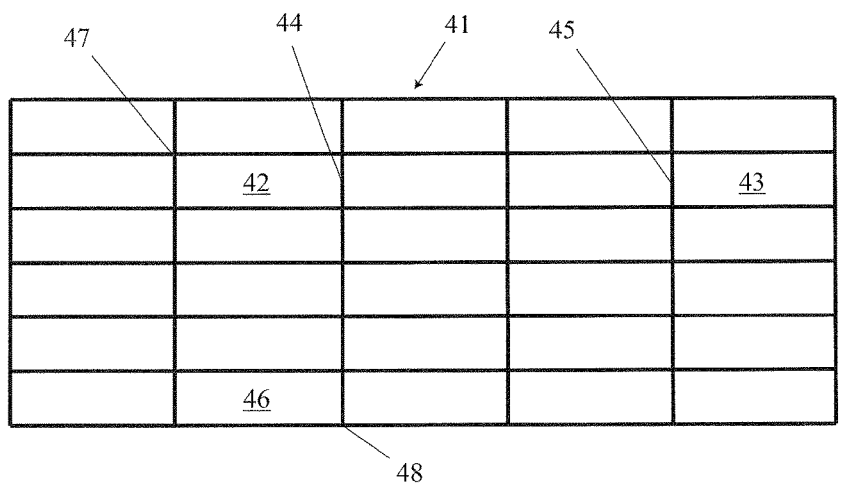
FIG. 4: Illustration of directional bias using a top view of a sensor array according to one embodiment with sensors having rectangular shape and 1:3 aspect ratio.

For a more complete understanding of directional bias, refer to the example illustrated in FIG. 4. FIG. 4 shows a top view of a sensor array 41 containing rectangular sensors that are binary detectors. That is, each sensor state, or status, indicates that either AN OBJECT IS PRESENT on, or over, the sensor or that NO OBJECT IS PRESENT on, or over, the sensor. Each sensor of sensor array 41 has the common width W=1 units of length and common length L=3 units of length. If an object moves a quantity q=3 sensors to the right from sensor 42 to sensor 43, then the pressure-sensing device identifies movement over at least four sensors. This indicates motion covering a distance at least $(q-1) \times L=6$ units of length; the least distance occurs when the object moves horizontally from the right edge 44 of sensor 42 to the left edge 45 of sensor 43. In contrast, if an object instead moves down q+1=4 sensors from sensor 42 to sensor 46, then the pressure-sensing device identifies movement over at least five sensors. However, despite the fact that more sensor state changes are triggered in the latter case, this represents motion covering a shorter net distance of at most $\sqrt{34}$ units of length. This is the net distance covered by an object that moves, for example, from corner 47 of sensor 42 to corner 48 of sensor 46. More generally, for rectangular shaped sensors of unequal side lengths with side length ratio r=W/L<1, the same distortion occurs for q satisfying $\sqrt{(W(q+2))^2+L^2}<(q-1)L$. Rewriting this in terms of the side length ratio gives the condition $(1-r^2)q^2-2(1+2r^2)q-4r^2>0$. Note that the left hand side of this inequality is a polynomial in the independent variable q with a positive polynomial discriminant $4(1+2r^2)^2+16(1-r^2)r^2$, so it has two real roots. If q is larger than both of these roots, then the polynomial on the left hand side of the inequality is positive. Thus, a rectangular array of the type pictured in FIG. 4 with enough sensors to allow motion across q sensors, where q is larger than both of these roots, will exhibit directional bias effects. This indicates that if the ratio r of side lengths is less than one, then increasing the number of sensors in the sensor array as manufacturing capabilities improve, in an effort to achieve more precise measurements of position and motion, will eventually produce directional bias effects. To reduce directional bias a highly symmetric sensor shape is used.

Dense Packing of Sensors on the Planar Substrate

In one embodiment, the sensors and signal lines are arranged to cover with sensors the largest possible fraction of planar substrate that is consistent with readily available manufacturing processes. This reduces the problem of holes, or blind spots, in the sensor array where the presence of an object on the sensor array is not detected. Thus, the sensor array is more effective at measuring position and motion. In geometry, the theoretical limit of entire coverage of the ideal plane with shapes, or tiles, is achievable with a tiling, or tessellation, whereby finitely many shapes replicated infinitely often and positioned appropriately, cover the entire plane without overlapping. More precisely, portions of the shape boundaries may be shared, as, for example, when two tiles share a common edge, but no overlap of positive area in the plane may occur. The realities of manufacturing can prevent reaching the theoretical limit of complete coverage of a planar substrate with sensor components. These realities include the need to separate electrically conductive connecting lines and sensors with enough distance to prevent short circuits and reduce electrical coupling, whereby one electrical signal leaks, or transfers, to a nearby electrical conductor. In another embodiment, the sensors and signal lines may be arranged without the goal of covering with sensors the largest possible fraction of planar substrate. Detection ability may merely be needed over certain regions of the planar substrate for the intended use applications for the sensor array. Consequently, allowing holes, or blind spots, in the sensor array may be acceptable in exchange for a reduction of manufacturing cost via a simplified assembly process and reduction in the quantity of materials used.

In one embodiment, the sensors are about the same size with the same regular convex polygon shape. The term "regular" here indicates that the sides of a sensor have the same length and the angles are equal in measure. This provides symmetry in the sensor shape that reduces directional bias in the sensor array. To facilitate a dense packing, or tight arrangement, of the sensors on the planar substrate where the sensors cover a large fraction of the planar substrate, the inventor selects a regular convex polygon shape that can tile, or tessellate, the plane. It is an established result from geometry that the equilateral triangle, square, and regular hexagon are the three shapes with this property.

Sensitivity and Sensor Shape

Figure 5:
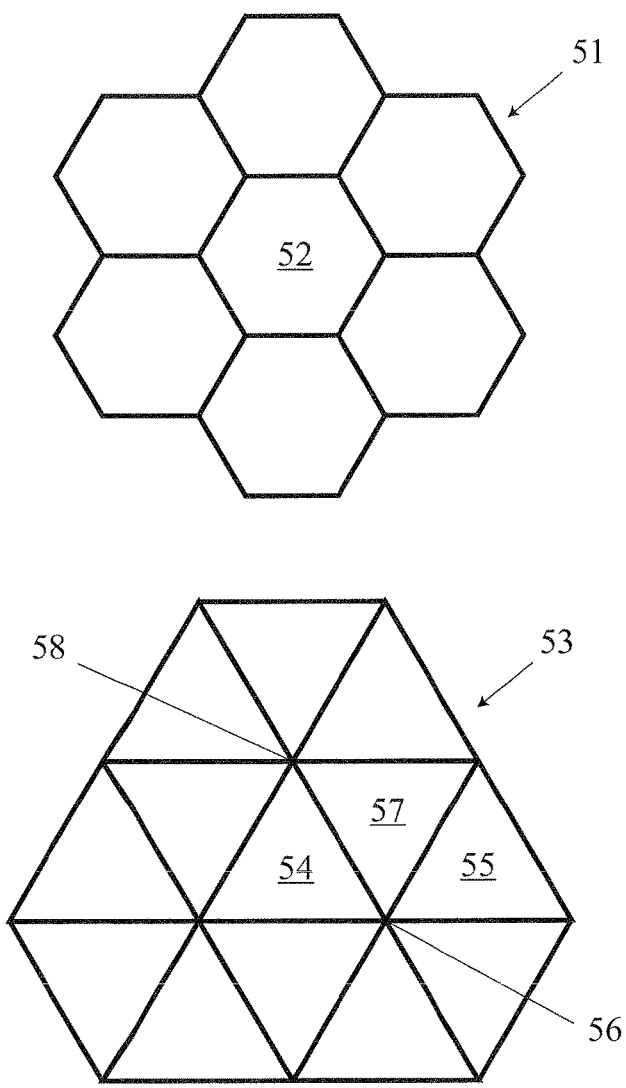
FIG. 5: Top view of neighboring sensors of a given sensor in embodiments using hexagonal and triangular sensor shapes.

In one embodiment, sensors have the shape of a regular hexagon. Alternatively, in another embodiment, the shape of a sensor may also be substantially circular, elliptical, triangular, square, rhombic, trapezoidal, quadrilateral, pentagonal, water drop shaped, or polygonal, but the present invention is not limited thereto. Of the regular convex polygon shapes that can tile the plane, the regular hexagon, compared to the equilateral triangle or square, offers better sensitivity in the sense described below for sensors that are binary detectors. Consider sensors that are binary detectors positioned on a planar substrate so that there is no overlapping of sensors and no space between sensors. If an object being monitored is detected over sensor H1, and then over a neighboring, or adjacent, sensor H2, the statement of how far the object moved is probabilistic, or uncertain, because the exact starting and ending positions are unknown. Sensors that are binary detectors simply indicate that the object is somewhere over sensor H1, and then, later, somewhere over the neighboring sensor H2, without providing information about the precise location of the object on each sensor. The inventor uses a uniform probability distribution, in the standard sense from mathematical probability and statistics, to describe, or model, the position of the object over H1. That is, for a given measure, or size, of area M, there is no bias that would cause the probability that the object is initially on one region of sensor H1 having area M to be different from the probability that the object is initially on a different region of sensor H1 having area M. The later position of the object over H2 is described, or modeled, in a similar manner. The inventor computes, using these uniform distributions, the expected value, in the standard sense from mathematical probability and statistics, of the distance between an arbitrary, or randomly, selected starting position on sensor H1 to an arbitrary, or randomly, selected ending position on sensor H2. $E[d_1]$ R denotes this expected value when sensors H1 and H2 have exactly one vertex, or corner, in common. $E[d_2]$ denotes this expected value when sensors H1 and H2 have exactly two vertices in common. A neighboring sensor may have 1 or 2 vertices in common with sensor H1. $E[d_{12}]$ denotes the expected value of the distance from an arbitrary starting position on sensor H1 to an arbitrary ending position on any of the neighboring sensors, where a uniform distribution is used to model the ending position on the collection, or union, of neighboring sensors. FIG. 5 clarifies the difference between two types of neighboring sensors. It illustrates the top view of the neighboring sensors 51 of a hexagonal sensor 52 in a sensor array and the neighboring sensors 53 of triangular sensor 54 in a different sensor array. Sensor 55 shares one vertex 56 with sensor 54. Sensor 57 shares both vertex 56 and vertex 58 with sensor 54.

Table 1 shows the results of the expected value computations for equilateral triangle, square, and regular hexagon sensor shapes. Each expected value is expressed in terms of, or as a function of, sensor side length s. Each expected value is also normalized for sensor area and expressed in terms of the sensor area A, where $A=s^2$ for a square, $A=\sqrt{3}s^2/4$ for an equilateral triangle, and $A=3\sqrt{3}s^2/2$ for a regular hexagon.

TABLE 1

Expected values for the distance between a position on one sensor and a position on a neighboring, or adjacent, sensor.

| Sensor Shape | $E[d_1]$ | $E[d_2]$ | $E[d_{12}]$ |
| --- | --- | --- | --- |
| Equilateral Triangle | 1.0909s | 0.6600s | 0.9832s |
|  | 1.6579$\sqrt{A}$ | 1.0029$\sqrt{A}$ | 1.4941$\sqrt{A}$ |
| Square | 1.4736s | 1.0881s | 1.2808s |
|  | 1.4736$\sqrt{A}$ | 1.0881$\sqrt{A}$ | 1.2808$\sqrt{A}$ |
| Regular Hexagon | *** | 1.8564s | 1.8564s |
|  |  | 1.1517$\sqrt{A}$ | 1.1517$\sqrt{A}$ |

When normalized for area, the hexagon shape provides the smallest expected distance, 1.1517$\sqrt{A}$, from a point on one sensor to a point on a neighboring sensor. When sensor array measurements indicate the presence of an observed object over a sensor, and, later, over a neighboring sensor, the expected value of the distance the object traveled is lowest when using the regular hexagon sensor shape. That is, the sensor array is, in this sense, more sensitive for measuring movement than a sensor array using square or equilateral triangle shaped sensors.

Directional bias exists, in a probabilistic sense, when the sensor shapes are equilateral triangles or squares. The expected distance for movement to a neighboring sensor sharing a single vertex is greater than that for movement to a neighboring sensor sharing two vertices. That is, $E[d_1]>E[d_2]$. In contrast, the hexagon shaped sensors do not produce this type of directional bias.

Flexible Substrates and Spacers

In one embodiment, the planar substrates are flexible with sensors designed to produce contact between a sensor component on one planar is substrate and a sensor component on a second planar substrate when a sufficient force is applied to one, or both, of the planar substrates by an object causing flexing, or bending, of one, or both, of the planar substrates. A plurality of spacers on, or between, the planar substrates maintain separation between the planar substrates in the absence of an applied force. However, when a force is applied near one or more spacers, these spacers may continue to maintain separation between the two planar substrates, preventing contact between a sensor component on one planar substrate and a sensor component on the other planar substrate, so that the sensor comprising these sensor components fails to indicate the presence of the force and the object applying it.

Figure 6:
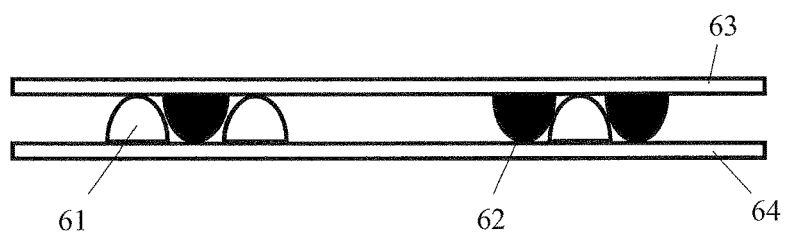
FIG. 6: Side view of spacers according to one embodiment of the present disclosure.

FIG. 6 shows spacers according to one embodiment of the present disclosure. In FIG. 6, spacers 61 and 62 are disposed between the second planar substrate 63 ($P_2$) and the first planar substrate 64 ($P_1$). The spacers 61 and 62 can be divided into first spacers 61 fastened on the first planar substrate 64 and second spacers 62 fastened on the second planar substrate 63, and the first spacers 61 and the second spacers 62 are coupled together, so as to prevent the sensor components $A_{i,j}$ and $B_{i,j}$ from misalignment.

Figure 7:
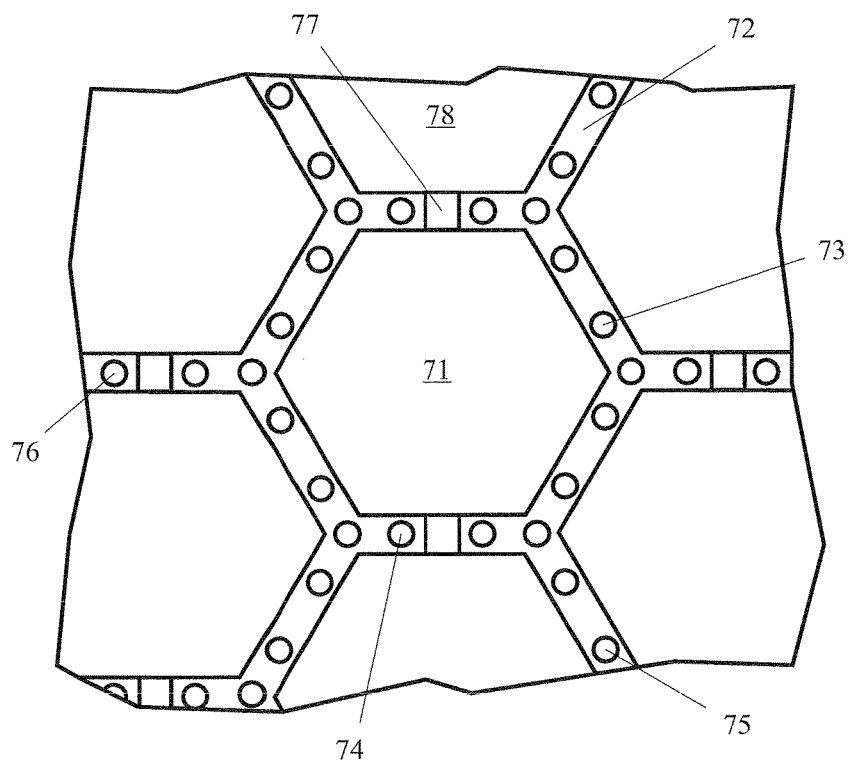
FIG. 7: Top view of spacers surrounding the perimeter of a sensor component according to one embodiment of the present disclosure.

In one embodiment, spacers are positioned around the perimeter, or boundary edges, of a sensor, but not in the interior of that sensor. FIG. 7 illustrates a top view of an arrangement of spacers around the perimeter of a sensor component. Sensor component 71 is one of a plurality of sensor components on a planar substrate 72. A total of 18 spacers, including spacer 73 and spacer 74, are positioned around the perimeter of sensor component 71. Additional spacers, including spacer 75 and spacer 76 surround the perimeters of sensor components that are neighbors of sensor component 71 Conductive connecting line 77 connects sensor component 71 to neighboring sensor component 78. In an alternative embodiment, spacers may be also be positioned in the interiors of sensors. This alternative embodiment has the advantage of enabling sensor components to be positioned closer together since an intervening space on the planar substrate between sensor components is not used to accommodate spacers. However, spacers positioned in the interior of a sensor may scrape, or abrade, against sensor components, so this should be considered in the positioning of spacers and the selection of materials for sensor components.

Edge Effect

Figure 8:
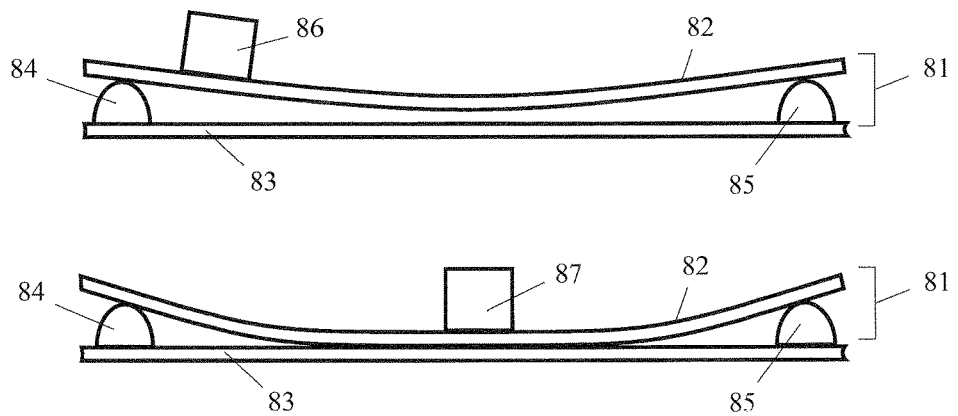
FIG. 8: Illustration of an "edge effect" using a side view of a pressure sensor in an array having a flexible planar substrate according to one embodiment of the present disclosure.

If spacers are positioned around the perimeter of a sensor, but not in the interior of that sensor, then there is an "edge effect", or "boundary effect", whereby the ability of the sensor to detect an object is reduced when the object is near the edges of the sensor. FIG. 8 illustrates the edge effect by showing a side view of a sensor 81. Sensor details such as electrically conductive connecting lines are not pictured to focus attention on the planar substrates. Flexible planar substrate 82 is separated from planar substrate 83 by spacers including spacer 84 and spacer 85. A force applied to planar substrate 82 by the weight of object 86, which is not part of the sensor, does not produce contact between the two planar substrates. However, the force applied to planar substrate 82 by the weight of object 87, which is not part of the sensor, positioned nearer the center of the sensor 81 cross section causes planar substrate 82 to flex a sufficient amount to produce contact between the two planar substrates.

Figure 9:
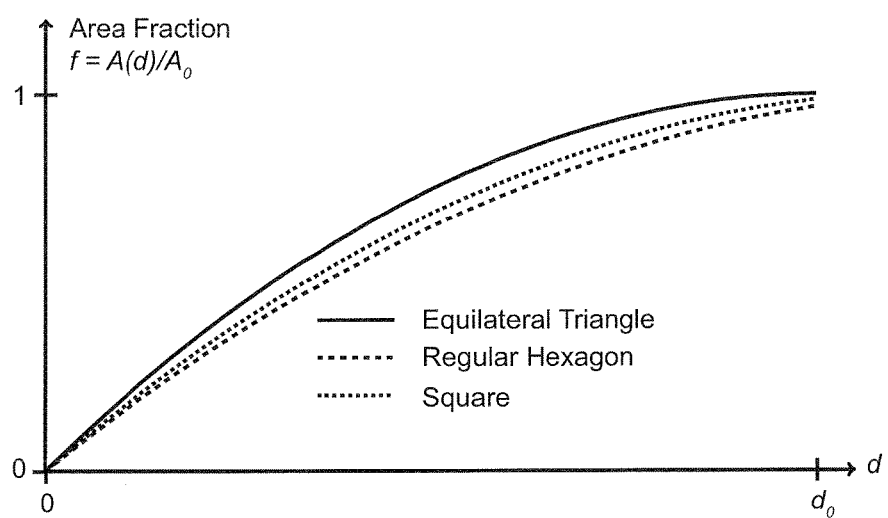
FIG. 9: Plots of the fraction of sensor surface area that is within a given distance from sensor edges presented for three sensor shapes.

The sensor shape influences the impact of the edge effect. The edge effect is less when the fraction, or part, of the sensor surface that is near the edges, and near the spacers, is smaller. Let $A_0$ be the surface area of a sensor. Let A(d) be the surface area of that part D of the interior of the sensor consisting of locations, or points, that are less than a distance d from an edge of the sensor. The inventor computes the area fraction $f=A(d)/A_0$ for the equilateral triangle, square, and regular hexagon shapes and finds it to be $f=4K(1-K)$ where $K=d\sqrt{N}/2\sqrt{A_0}\tan(\pi/2-\pi/N)$ and N is the number of sensor edges. The inventor also finds that the condition $0<d<d_0$ where $$d_0 = \sqrt{A_0} \bigg/ \sqrt{3\sqrt{3}}$$

ensures that d is not so large that D contains the center of the sensor for any of the three shapes and that the area fraction f for the regular hexagon shape is smaller than the area fractions for the two other shapes. This fact is presented in graphical form in FIG. 9 where the area fraction f is plotted as a function of distance d. Thus, a sensor with a regular hexagon shape will exhibit less edge effect than a sensor of the same area and materials having a square shape or an equilateral triangle shape.

Signal Lines and Connecting Lines

Signal lines on the planar substrates connect each sensor to a scanning unit and to a measuring unit. The scanning unit provides power to sensors via an applied electric potential and electric current that varies in a manner determined by the scanning unit control circuitry and programming. For example, power may be simultaneously provided, for a predetermined duration, to the sensor components in a first row of sensor components on the first planar substrate. Subsequently, the power may be applied to sensor components in a second row of sensor components, a third row of sensor components, etc. until each row has been provided power for a predetermined duration, after which the process repeats. The scanning unit, and the measuring unit, may be affixed directly to the planar substrates. Alternatively, the signal lines may connect to the scanning unit and measuring unit via intervening wires, plugs, sockets, interconnects, adapters, cable assemblies, and related electrical connecting apparatuses.

Connections between signal lines and sensor components may not be direct. In particular, a plurality of intervening, or intermediate, electrically conductive sensor components and connecting lines may assist to transfer electrical power from the scanning unit to a sensor and to transfer sensor data from a sensor to the measuring unit. Surface regions on the planar substrates used for signal lines are not available for placing sensors. Thus, these regions are holes, or blind spots, where the sensor array can not detect the presence of an observed object. One advantage of utilizing intermediate electrically conductive sensor components and conducting lines to connect sensors to the signal lines is that this enables the use of fewer signal lines because each signal line may be shared by multiple sensor components. A second advantage is that this enables the use of shorter signal lines, because each signal line merely needs to connect to one of the multiple sensor components that share it. Surface regions on the planar substrates used for connecting lines are also not available for placing sensors. Consequently, the inventor acts to reduce the fraction of the planar substrate surface used for either signal lines or connecting lines.

In one embodiment, signal lines, connecting lines, and some of the electrically conductive sensor components may be formed from a conductive paint, or ink, applied to, or printed on, planar substrates. The conductive paint may include a combination of electrically conductive metallic particles containing a mixture of carbon, silver, or other elements, as well as adhesives that enable bonding to planar substrates. Properties of the conductive paint and its application affect sensor array durability. These properties include the choice of metallic particles, the adhesive compound, the blending proportions of conductive paint ingredients, the thicknesses, or heights, of painted signal lines, connecting lines, and additional sensor components, and the widths of signal lines and connecting lines. These properties can be selected so that conductive paint resists chipping, breaking, or flaking off from a planar substrate under repeated flexing.

Sensor Component Structure

In one embodiment, each sensor component comprises patterns of electrically conductive paint, or ink, printed on a planar substrate. An advantage of this embodiment is that it provides a method of fabricating sensors which is less expensive than using some other types of pressure sensors, such as piezoelectric or micro-electromechanical systems (MEMS) pressure sensors. On the other hand, a disadvantage of this embodiment is that a sensor may be limited to two states. In particular, a sensor's state may be determined by whether or not there is physical contact between the conductive paint of a sensor component on the first planar substrate and the conductive paint of a sensor component on the second planar substrate.

Figure 10:
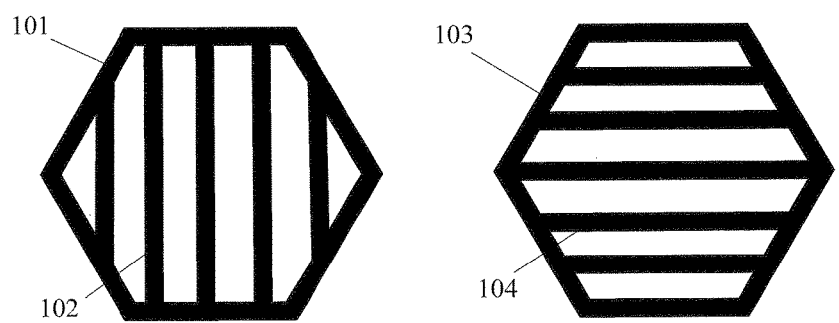
FIG. 10: Top view of sensor components according to one embodiment of the present disclosure.

FIG. 10 shows the structure of sensor components according to one is embodiment of the present disclosure. On the first planar substrate $P_1$, the component includes a first conductive loop 101 and a plurality of first conductive lines 102. The first conductive loop 101 is formed on the first planar substrate $P_1$. The first conductive lines 102 are disposed within and connected to the first conductive loop 101, and arranged in a first direction (e.g., a column direction). On the second planar substrate $P_2$, the sensor component includes a second conductive loop 103 and a plurality of second conductive lines 104. The second conductive loop 103 is formed on the second planar substrate $P_2$. The second conductive lines 104 are disposed within and connected to the second conductive loop 103, and arranged in a second direction (e.g., a row direction) that may be different from the first direction for improving sensitivity and reducing the amount of conductive material printed on the planar substrates. Alternatively, in another embodiment, the first conductive lines and second conductive lines may be curved, or angled, or wavy, and may have sufficient width, and may be present in sufficient number that they fill the first conductive loop or the second conductive loop, but the present invention is not limited thereto.

Charge Relaxation Time

The materials used to fabricate signal lines, connecting lines, and additional sensor components may be selected for their abilities to bond to the planar substrate. While establishing a bond and maintaining it over time subject to flexion, abrasion, and environmental conditions consistent with normal, and even abnormal, use are advantageous, some electrical properties may be sacrificed. In particular, the signal lines, connecting lines, and additional sensor components may not be uniform electrical conductors. For example, the depth of a conducting paint layer will vary with the position on the planar substrate as will the distribution of electrically conductive metallic particles blended with non-conducting adhesive and other compounds in the paint. The non-uniform distribution of conducting metallic particles may create capacitive effects on a microscopic scale. Moreover, there may be variations in current flow and charge density across and conductor after a potential difference, or voltage, is applied. This may be coincident with a complex set of electric fields within the conductor as well as variations in the magnetic fields produced by the electric currents. To compensate for these effects, a charge relaxation time $t_r$ is included after each reading of sensor states. This provides an interval during which energy stored within electric and magnetic fields can be released and local concentrations of electric charge in the conducting paint can dissipate.

Sensor Array with Two Planar Substrates Having Different Layouts

In one embodiment, the biplanar sensor array in a pressure sensor pad is fabricated using first planar substrate $P_1$ and second planar substrate $P_2$ having different arrangements, or layouts, of signal lines and connecting lines leading to, or from, the sensor components. During assembly, $P_2$ is disposed, or positioned, opposite to $P_1$, as shown in FIG. 1. The arrangement of sensor components and signal lines is now described.

$P_1$ contains a matrix, or grid-like, pattern of m rows of n sensor components of a first type, or "first sensor components", labeled $A_{i,j}$ where $1 \leq i \leq m$ and $1 \leq j \leq n$. The rows of first sensor components on $P_1$ are labeled, or indexed, from top to bottom. The individual first sensor components in each row are labeled from left to right. Thus, $A_{1,1}$ is in the upper left corner of the array. The sensor components $A_{i,j}$ in a row specified by one particular index i are connected to a common signal line $S_i$ of a first type, or "first signal line". $S_i$ is a select line that is connected to a scanning unit. At any time, the scanning unit provides an electric potential and current to at most one of the select lines. That is, at any time, it selects at most one row of sensors to which it provides power for the purpose of enabling sensor state measurements.

$P_2$ contains a matrix pattern of n columns of m sensor components of a second type, or "second sensor components", labeled $B_{i,j}$ where $1 \leq i \leq m$ and $1 \leq j \leq n$. The columns of second sensor components on $P_2$ are labeled, or indexed, from right to left. The individual second sensor components in each column are labeled from top to bottom. Thus, $B_{1,1}$ is in the upper right corner of the array. The sensor components $B_{1,1}$ in a column specified by a single index j are connected to a common signal line $R_j$ of a second type, or "second signal line". $R_j$ is a read line that is connected to a measuring unit. The measuring unit detects electric current or voltage changes on the read line to determine the state of a selected sensor. In an alternative embodiment, the first signal lines may be read lines, and the second signal lines may be select lines.

Each sensor component on $P_1$ is connected to at most two other sensor components that are neighboring, or adjacent, to it in the same row. In each row, one sensor component at an end of the row is connected to a select line and each of the remaining sensor components in the row is connected to the neighboring sensor component in the row that is nearer to the select line. Similarly, each sensor component on $P_2$ is connected to at most two other sensor components that are neighboring, or adjacent, to it in the same column. In each column, one sensor component at an end of the column is connected to a read line and each of the remaining sensor components in the column is connected to the neighboring sensor component in the column that is nearer to the read line. A total of m+n signal lines are connected to the scanning unit and measuring unit. This is fewer signal lines than is used for some other possible arrangements of signal lines and connecting lines on the planar substrates. For example, if each sensor has its own read line and select line, then 2 mn signal lines are used. Alternatively, if each sensor has its own read line and one common select line simultaneously provides power to all sensors, then mn+1 signal lines are used.

Figure 11:
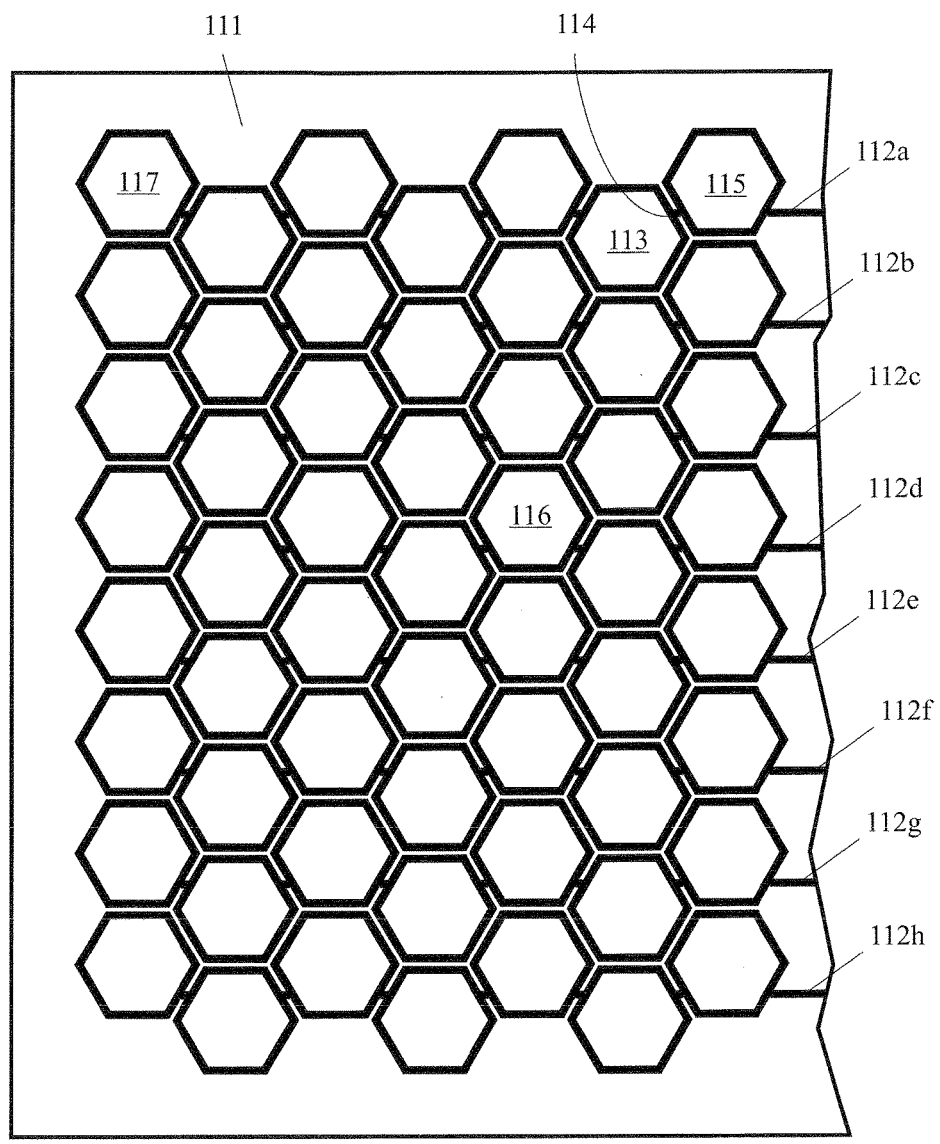
FIG. 11: Top view of planar substrate $P_1$ in accordance with one embodiment of the present disclosure that allows an 8×7 biplanar sensor array having different arrangements of signal lines and connecting lines on two planar substrates.
Figure 12:
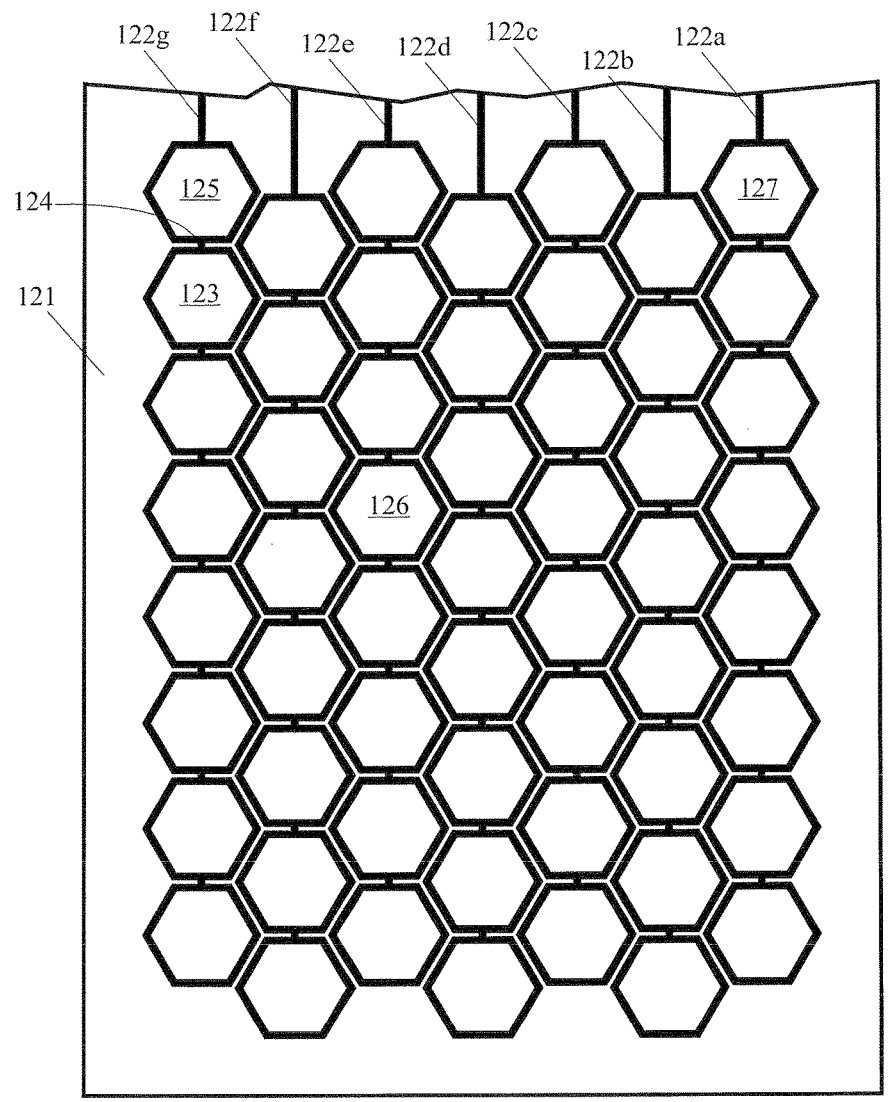
FIG. 12: Top view of planar substrate $P_2$ in accordance with the embodiment depicted in FIG. 11.

FIGS. 11 and 12 illustrate the two planar substrates for a pressure sensor pad with m=8 rows and n=7 columns of sensors. The arrangement of signal lines and connecting lines is different on the two planar substrates. FIG. 11 presents a top view of planar substrate 111 ($P_1$) with m=8 rows of hexagonal first sensor components connected to first signal lines 112a, 112b, 112c, 112d, 112e, 112f, 112g, and 112h, which are select lines $S_1, \ldots, S_8$. FIG. 11 shows 56 first sensor components, including first sensor component 113, which is connected to select line 112a ($S_1$) via intervening connecting line 114 and first sensor component 115. First sensor component 116 is denoted $A_{4,5}$ and first sensor component 117 is denoted $A_{1,1}$.

FIG. 12 presents a top view of second planar substrate 121 ($P_2$) with n=7 columns of second sensor components connected to second signal lines 122a, 122b, 122c, 122d, 122e, 122f, and 122g, which are read lines $R_1, \ldots, R_7$. FIG. 12 shows 56 second sensor components, including second sensor component 123, which is connected to read line 122g ($R_7$) via intervening connecting line 124 and second sensor component 125. Second sensor component 126 is denoted $B_{4,5}$ and second sensor component 127 is denoted $B_{1,1}$.

In FIGS. 11 and 12, the first signal lines $S_1, \ldots, S_8$ are select lines and the second signal lines $R_1, \ldots, R_7$ are read lines. In an alternative embodiment, the first signal lines are read lines, and the second signal lines are select lines.

During assembly, second planar substrate 121 is rotated 180 degrees about the vertical central axis that passes through the column of sensors connected to read line 122d. It is then disposed, or positioned, opposite, or on top of, first planar substrate 111 sandwiching the sensor components between the two planar substrates. Alignment of the planar substrates is adjusted so that first sensor component 117 ($A_{1,1}$) faces second sensor component 127 ($B_{1,1}$); these are sensor components of sensor $S_{1,1}$. Similarly, first sensor component 116 ($A_{4,5}$) faces second sensor component 126 ($B_{4,5}$); these are sensor components of sensor $S_{4,5}$.

The read lines and select lines are used together to determine sensor states. A read algorithm for one embodiment may be implemented as described herein. The voltage, or electric potential, of read lines is held low at $V_L$. When the voltage applied to a select line $S_i$, where $1 \leq i \leq m$, is pulled high, or raised, to $V_H$ by a scanning unit for a read interval duration $t_h$, the states of n sensors $S_{i,j}$, where $1 \leq j \leq n$, can be read by a measuring unit by measuring electric currents flowing on read lines $R_1$, where $1 \leq j \leq n$. For example, during the read interval when the voltage is raised on select line $S_4$, while voltage is being held low on read line $R_5$, creating a potential difference $V_H - V_L$ between the two sensor components $A_{4,5}$ and $B_{4,5}$, the current on read line $R_5$ indicates the state of sensor $S_{4,5}$. Table 2 summarizes this information. By raising the electric potential applied to select lines $S_1, \ldots, S_m$ in succession, so that at any time the voltage of at most one select line is raised high, it is possible to read the states of all array elements.

TABLE 2

The states of n sensors can be read during each time interval when the voltage of a single select line $S_i$ is raised to $V_H$.

| Raise potential of select line $S_i$ | Measure current on read lines | Determine states of sensors |
|---|---|---|
| $1 \leq i \leq m$ | $R_1, \ldots, R_n$ | $S_{i,j}$ where $1 \leq j \leq n$ |

Figure 13:
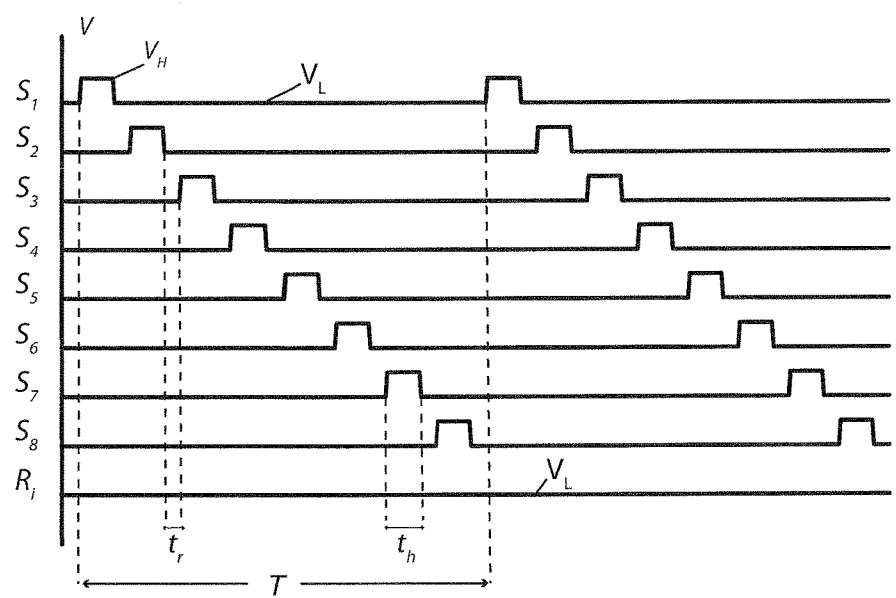
FIG. 13: Timing diagram for read line and select line voltages in accordance with the embodiment depicted in FIGS. 11 and 12.

When a charge relaxation time $t_r$ is included between read intervals used for measuring current on read lines, the time used to read the states of all array sensors is $T = m(t_h + t_r)$. By continually repeating this process a read cycle for the entire sensor array can be implemented having time period T. FIG. 13 presents a timing diagram consistent with this read algorithm for the case of an 8×7 sensor array. If, for example, each select line is held high for read interval duration $t_h$=10 ms (milliseconds) and a relaxation time of $t_r$=2.5 ms is allowed, then the entire array can be read in time period T=100 ms. Actual time durations selected for any particular array will depend on the material properties of sensor array electrical conductors as well as the control circuitry of the scanning unit and measuring unit.

Sensor Array with Two Planar Substrates Having Identical Layouts

In one embodiment, the biplanar sensor array in a pressure sensor pad is fabricated using planar substrate $P_1$ and planar substrate $P_2$ having identical arrangements, or layouts, of signal lines and connecting lines leading to, or from, the sensor components. This offers the advantage of potentially reducing the cost to produce a complete sensor array by simplifying the manufacturing process. The arrangement of sensor components in a grid-like pattern is the same as in the embodiment described previously where the sensor array is constructed from two planar substrates having different layouts, but the positions of signal lines and connecting lines are altered, as is the read algorithm.

If each sensor consists of two sensor components of identical, or nearly identical structure, such as a pattern of conducting material painted, or printed, on a flexible planar substrate, then it is possible to create a sensor array combining two planar substrates with identical arrangements of sensor components, signal lines, and connecting lines. Nevertheless, the read lines and select lines on these planar substrates should be differentiated in the description of the sensor array because they are physically distinct electrical conductors. Each planar substrate holds signal lines that function as read lines as well as signal lines that function as select lines. The inventor designs for the case where the number of columns n is an odd integer at least three, so n=2k+1 for some positive integer k. The sensor array is assembled by joining the two planar substrates $P_1$ and $P_2$ as illustrated in FIG. 1.

The arrangement of a first matrix array of sensor components and signal lines on the first planar substrate $P_1$ is now described. The description is subdivided into descriptions of the arrangement on the right side of $P_1$ and the arrangement on the left side of $P_1$. The right side of $P_1$ contains m rows of k+1 sensor components of a first type, or "first sensor components", labeled $A_{i,j}$ where $1 \le i \le m$ and $k+1 \le j \le n$. Sensor components are labeled so that index i increases from top to bottom and index j increases from left to right along any row. The sensor components $A_{i,j}$ in a row specified by one particular index i are connected to a common signal line $S_i$ of a first type, or "first signal line". $S_i$ is a select line that is connected to both a scanning unit and a measuring unit. The left side of $P_1$ contains k columns of m sensor components of a second type, or "second sensor components", labeled $B_{i,j}$ where $1 \le i \le m$ and $1 \le j \le k$. The columns of second sensor components are disconnected from the rows of first sensor components. Sensor components are labeled so that the index i increases from top to bottom and index j increases from left to right across the columns. The sensor components $B_{i,j}$ in a column specified by a single index j are connected to a common signal line $R_j$ of a second type, or "second signal line". The second signal lines are disconnected from the first signal lines. $R_j$ is a read line that is connected to a measuring unit.

The arrangement of a second matrix array of sensor components and signal lines on the second planar substrate $P_2$ is now described. The description is subdivided into descriptions of the arrangement on the right side of $P_2$ and the arrangement on the left side of $P_2$. The right side of $P_2$ contains m rows of k+1 sensor components of a third type, or "third sensor components", labeled $A_{i,j}$ where $1 \le i \le m$ and $1 \le j \le k+1$. Sensor components are labeled so that index i increases from top to bottom and index j increases from right to left across any row. The sensor components $A_{i,j}$ in a row specified by one particular index i are connected to a common signal line $S_{i+m}$ of a third type, or "third signal line". $S_{i+m}$ is a select line that is connected to both a scanning unit and a measuring unit. The left side of $P_2$ contains k columns of m sensor components of a fourth type, or "fourth sensor components", labeled $B_{i,j}$ where $1 \le i \le m$ and $k+2 \le j \le n$. The columns of fourth sensor components are disconnected from the rows of third sensor components. Sensor components are labeled so that index i increases from top to bottom and index j increases from right to left across the columns. The sensor components $B_{i,j}$ in a column specified by a single index j are connected to a common signal line $R_j$ of a fourth type, or "fourth signal line". The fourth signal lines are disconnected from the third signal lines. $R_j$ is a read line that is connected to a measuring unit.

Each first (or third) sensor component is connected to at most two other sensor components via connecting lines; these are the first (or third) sensor components that are neighboring, or adjacent, to it in the same row. In each row, one first (or third) sensor component at an end of the row is connected to a select line and each of the remaining first (or third) sensor components in the row is connected to the neighboring first (or third) sensor component in the row that is nearer to the select line.

Each second (or fourth) sensor component is connected to at most two other sensor components via connecting lines; these are the second (or fourth) second sensor components that are neighboring, or adjacent, to it in the same column. In each column, one second (or fourth) sensor component at an end of the column is connected to a read line and each of the remaining second (or fourth) sensor components in the column is connected to the neighboring second (or fourth) sensor component in the column that is nearer to the read line.

Note how the indices used to label read and select lines in $P_2$ differ from those used to label read and select lines in $P_1$. Also note that there is no read line $R_{k+1}$. The sensors in the middle column are read by measuring current on select lines, each of which is called into "double duty" playing the typical role of a read line for at least one read time interval in each read cycle. A total of 2m+n−1 signal lines are connected to the scanning unit and measuring unit. When m is larger than 1, this is more than the number of signal lines, m+n, for the previously described sensor array, which has different arrangements of signal lines and connecting lines on the two planar substrates.

During assembly, the second planar substrate is disposed, or positioned, opposite to the first planar substrate, as shown in FIG. 1. The second matrix array of sensor components faces the first matrix array of sensor components respectively, and an arrangement of the first signal lines, the second signal lines and the first matrix array is equal to an arrangement of the third signal lines, the fourth signal lines and the second matrix array. The sensor components are arranged on the planar substrates in such a manner that sensor components $A_{i,j}$ and $B_{i,j}$ face each other for any i satisfying $1 \le i \le m$ and for any j satisfying $1 \le j \le n$.

Figure 14:
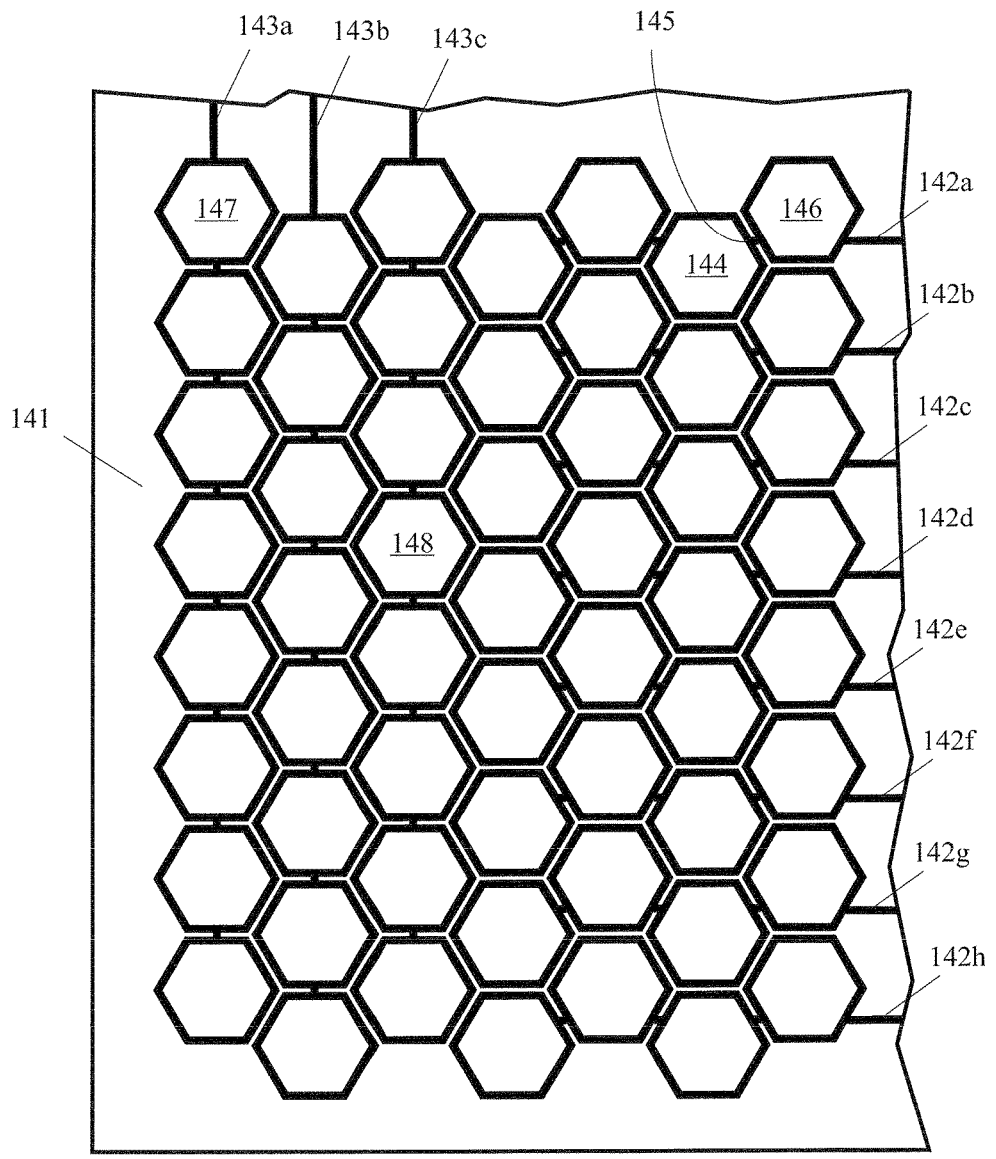
FIG. 14: Top view of planar substrate $P_1$ in accordance with one embodiment of the present disclosure that allows an 8×7 biplanar sensor array having identical arrangements of signal lines and connecting lines on two planar substrates.
Figure 15:
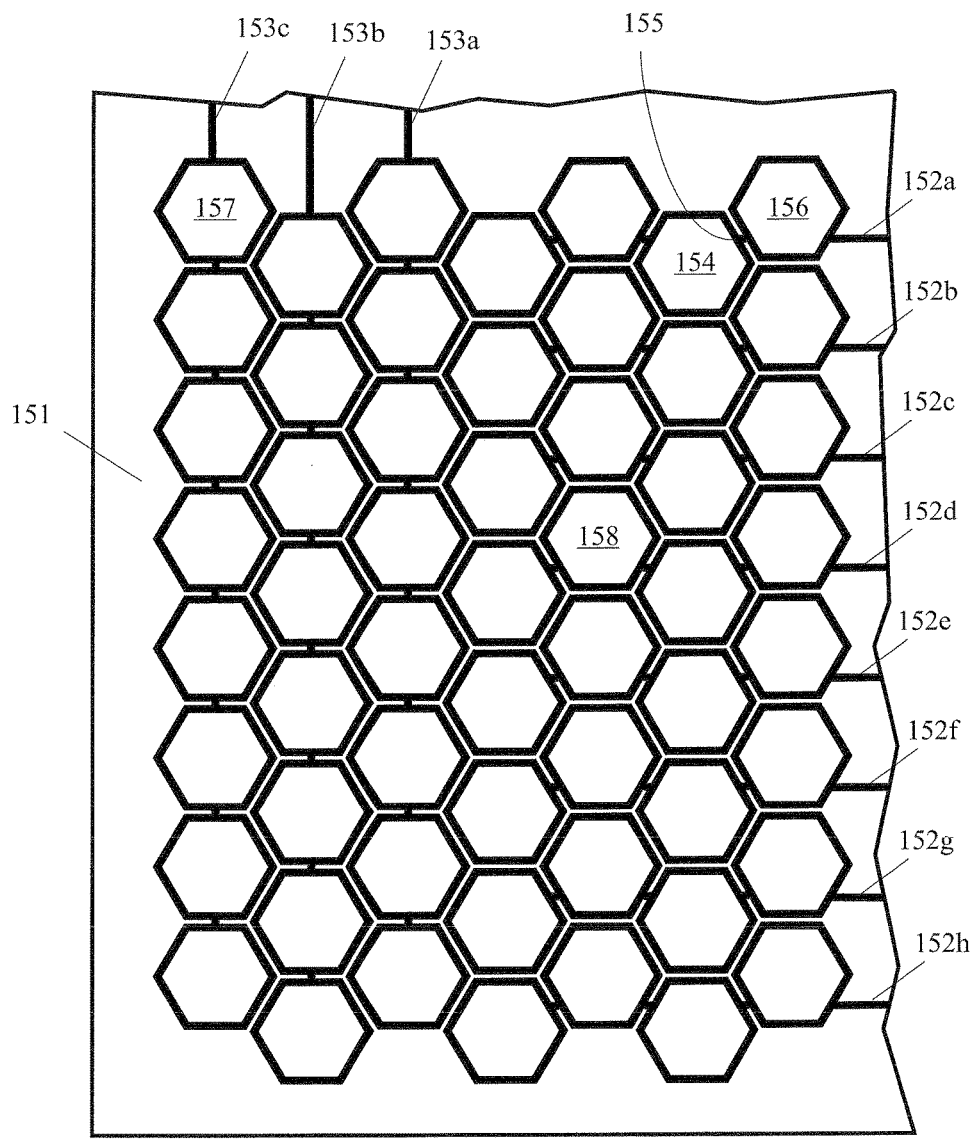
FIG. 15: Top view of planar substrate $P_2$ in accordance with the embodiment depicted in FIG. 14.

FIGS. 14 and 15 illustrate the two planar substrates for a pressure sensor pad with m=8 rows and n=7 columns of sensors. The arrangement of signal lines and connecting lines is the same on the two planar substrates.

FIG. 14 presents a top view of planar substrate 141 ($P_1$) and a first matrix array of sensor components. $P_1$ has m=8 rows of hexagonal first sensor components connected to first signal lines 142a, 142b, 142c, 142d, 142e, 142f, 142g, and 142h, which are select lines $S_1, \ldots, S_8$. In addition, $P_1$ has k=3 columns of hexagonal second sensor components connected to second signal lines 143a, 143b, and 143c, which are read lines $R_1$, $R_2$, and $R_3$. FIG. 14 shows 56 first sensor components, including first sensor component 144, which is connected to select line 142a ($S_1$) via intervening connecting line 145 and first sensor component 146. First sensor component 146 is denoted $A_{1,7}$, second sensor component 147 is denoted $B_{1,1}$, and second component 148 is denoted $B_{4,3}$.

FIG. 15 presents a top view of planar substrate 151 ($P_2$) and a second matrix array of sensor components. $P_2$ has m=8 rows of hexagonal third sensor components connected to third signal lines 152a, 152b, 152c, 152d, 152e, 152f, 152g, and 152h, which are select lines $S_9, \ldots, S_{16}$. In addition, $P_2$ has k=3 columns of hexagonal fourth sensor components connected to fourth signal lines 153a, 153b, and 153c, which are read lines $R_5$, $R_6$, and $R_7$. FIG. 15 shows 56 first sensor components, including third sensor component 154, which is connected to select line 152a ($S_1$) via intervening connecting line 155 and third sensor component 156. Third sensor component 156 is denoted $A_{1,1}$, fourth sensor component 157 is denoted $B_{1,7}$, and third component 158 is denoted $A_{4,3}$.

During assembly, second planar substrate 151 is rotated 180 degrees about the vertical central axis that passes through the center of the second matrix array parallel to the columns of fourth sensor components. It is then disposed, or positioned, opposite, or on top of, first planar substrate 141 sandwiching the sensor components between the two planar substrates. Alignment of the planar substrates is adjusted so that third sensor component 156 ($A_{1,1}$) faces second sensor component 147 ($B_{1,1}$); these are sensor components of sensor $S_{1,1}$. Similarly, third sensor component 158 ($A_{4,3}$) faces second sensor component 148 ($B_{4,3}$); these are sensor components of sensor $S_{4,3}$. Also, fourth sensor component 157 ($B_{1,7}$) faces first sensor component 146 ($A_{1,7}$); these are sensor components of sensor $S_{1,7}$.

In FIGS. 14 and 15, the second and fourth signal lines $R_1$, $R_2$, $R_3$, $R_5$, $R_6$, and $R_7$ are read lines, and the first and third signal lines $S_1, \ldots, S_{16}$ are select lines. In an alternative embodiment, the second and fourth signal lines are select lines, and the first and third signal lines are read lines.

The read lines and signal lines are used together to determine sensor states. A read algorithm for one embodiment may be implemented as described herein. The voltage, or electric potential, of read lines is held low at $V_L$.

When the voltage applied to a select line $S_i$, where $1 \le i \le m$, is pulled high, or raised, to $V_H$ by a scanning unit for a read interval duration $t_h$, the states of k+1 sensors can be read. In particular, the states of k sensors $S_{i,j}$, where $k+2 \le j \le n$, can be read by a measuring unit by measuring electric currents flowing on read lines $R_j$, where $k+2 \le j \le n$. Also, the state of one sensor $S_{i,k+1}$ can be read by measuring electric current flowing on select line $S_{i+m}$.

Similarly, when the voltage applied to a select line $S_i$, where $m+1 \le i \le 2m$, is pulled high to $V_H$ by a scanning unit for a read interval duration $t_h$, the states of k+1 sensors can be read. In particular, the states of k sensors $S_{i-m,j}$, where $1 \le j \le k$, can be read by a measuring unit by measuring electric currents flowing on read lines $R_j$, where $1 \le j \le k$. Also, the state of one sensor $S_{i-m,k+1}$ can be read by measuring electric current flowing on select line $S_{i-m}$.

Any sensor $S_{i,k+1}$, where $1 \le i \le m$, is in the middle column of the sensor array. It can be read by measuring current on $S_{i+m}$ when select line $S_i$ is held high at $V_H$. Or, it can be can be read by measuring current on $S_i$ when select line $S_{i+m}$ is held high at $V_H$. Thus, in each read cycle, during which all 2m select lines are pulled high in succession, there are two opportunities to read the state of each sensor in the middle column of the sensor array. One of these two measurements may simply be discarded. The select lines here have a double duty of providing power via a raised electric potential as well as carrying sensor state information via electric current. This is most easily accomplished when the measuring unit and scanning unit are implemented by a common unified set of control circuitry.

Table 3 provides a summary indicating, for each select line $S_i$, which read lines and select line are read. By raising the electric potential applied to select lines $S_1, \ldots, S_{2m}$ in succession in one read cycle, so that during any read interval the voltage of at most one select line is raised high, it is possible to read the states of all array elements. Observe that during one read cycle k+1 sensors can be read during each of the 2m read intervals and that one duplicate reading of each of the m sensors $S_{i,k+1}$, where $1 \le i \le m$, may be discarded. Thus, during one read cycle this read algorithm determines the states of 2m(k+1)−m=m(2k+1)=mn sensors, which is the number of sensors in the array.

TABLE 3

The states of k + 1 sensors can be read during each read interval when the voltage of a single select line $S_i$ is raised to $V_H$.

| Raise potential of $S_i$ to $V_H$ | Measure current on lines | Determine states of sensors |
|---|---|---|
| $1 \le i \le m$ | $R_{k+2}, \ldots, R_n, S_{i+m}$ | $S_{i,j}$ where $k + 1 \le j \le n$ |
| $m + 1 \le i \le 2m$ | $R_1, \ldots, R_k, S_{i-m}$ | $S_{i-m,j}$ where $1 \le j \le k + 1$ |

Figure 16:
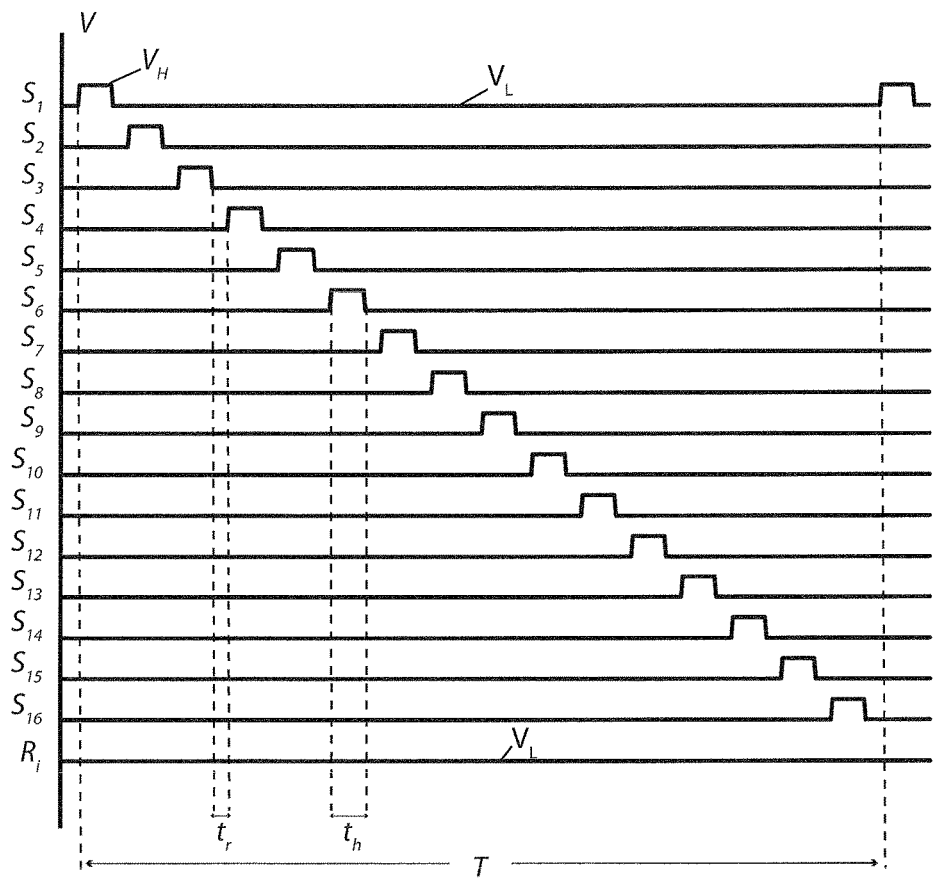
FIG. 16: Timing diagram for read line and select line voltages in accordance with the embodiment depicted in FIGS. 14 and 15.

When a charge relaxation time $t_r$ is included between read intervals used for measuring current on read lines, the time used to read the states of all array sensors is $T=2m(t_h+t_r)$. By continually repeating this process a read cycle for the entire sensor array can be implemented having time period T. FIG. 16 presents a timing diagram consistent with this read algorithm for the case of an 8×7 sensor array. If, for example, each select line is held high for read interval duration $t_h$=10 ms (milliseconds) and a relaxation time of $t_r$=2.5 ms is allowed, then the entire array can be read in time period T=200 ms.

Figure 17:
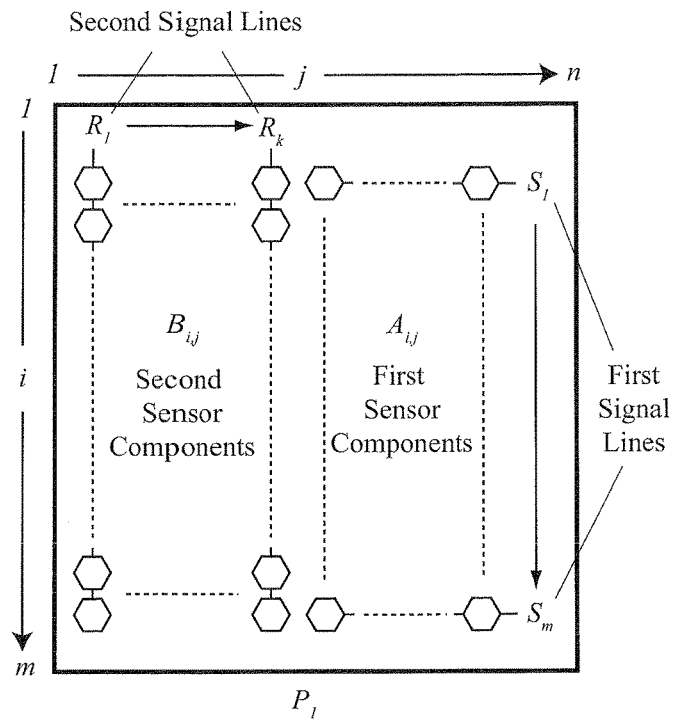
FIG. 17: Summary of notation used to describe the embodiment depicted in FIGS. 14 and 15.
Figure 17:
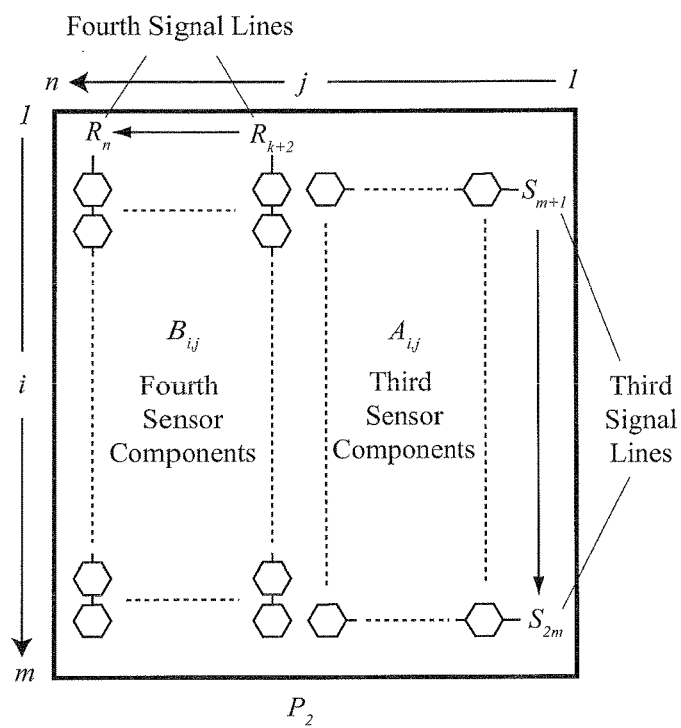

The arrangement and labeling of sensor components and signal lines in this embodiment may become better understood by referring to FIG. 17. FIG. 17 summarizes the notation used for sensor components and signal lines on $P_1$ and $P_2$; this includes an indication of the direction in which each index increases.

While using the same arrangement of signal lines and read lines on the two planar substrates may reduce manufacturing costs, a potential disadvantage in some use cases is that the read frequency is half of that provided by the embodiment using different arrangements of signal lines and connecting lines on the two planar substrates, using the same values of $t_h$ and $t_r$. Consequently, the read frequency should be considered when selecting a pressure sensor device embodiment for a particular application. In addition the cost advantages for different embodiments should be considered. Fabricating a single arrangement of signal lines and connecting lines on planar substrates may decrease production cost. On the other hand, manufacturing simpler scanning unit and measuring unit control circuitry for a sensor array that uses different arrangements of signal lines and connecting lines on the two planar substrates, and does not use "double duty" functionality on the part of select lines, may also decrease production cost.

Pressure-sensing Device

Figure 18:
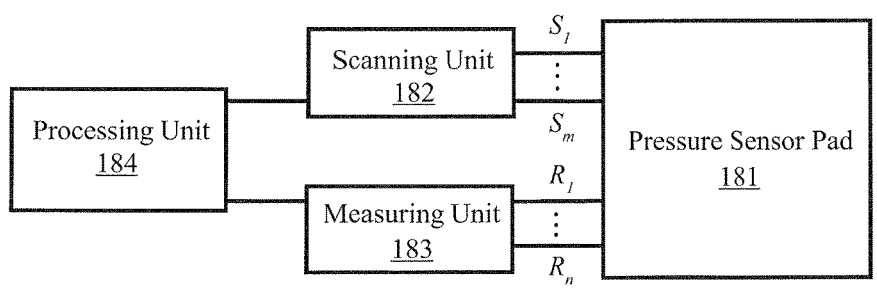
FIG. 18: Block diagram illustrating a pressure-sensing device according to one embodiment of the present disclosure.

FIG. 18 shows a pressure-sensing device according to one embodiment of the present disclosure. In FIG. 18, the pressure-sensing device includes a pressure sensor pad 181, a scanning unit 182, a measuring unit 183 and a processing unit 184. The scanning unit 182 can periodically scan the select lines $S_1, \ldots, S_m$ one by one. The measuring unit 183 can measure the resulting electric signals, such as current or voltage changes, on the read lines $R_1, \ldots, R_n$. The processing unit 184 can detect a pressure state of each of the pressure sensors of the pressure sensor pad 181 based on the resulting electric signals. In addition, when any one of the resulting electric signals is relatively low, the pressure state of a corresponding one of the pressure sensors is an OFF state; when any one of the resulting electric signals is relatively high, the pressure state of a corresponding one of the pressure sensors is an ON state.

When a patient lies on the pressure sensor pad 181, the processing unit 184 calculates variations of the resulting electric signals to analyze the body position and motion of the patient.

In one embodiment, the connection between the processing unit and the scanning unit is wireless, and the connection between the processing unit and the measuring unit is wireless. Additionally or alternatively, a wired connection is configured between the processing unit and the scanning unit, and another wired connection is configured between the processing unit and the measuring unit.

The scanning unit 182, the measuring unit 183 and the processing unit 184 may be hardware, software, and/or firmware. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

ADDITIONAL INFORMATION

The reader's attention is directed to all papers and documents which are filed concurrently with his specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C. § 112, 6th paragraph. In particular, the use of "step of" in the claims herein is not intended to invoke the provisions of 35 U.S.C. § 112, 6th paragraph.

What is claimed is:

1. A pressure-sensing device comprising;
a pressure sensor pad comprising:
a first planar substrate;
a plurality of first signal lines formed on the first planar substrate;
a plurality of second signal lines formed on the first planar substrate;
a first matrix array of sensor components formed on the first planar substrate, wherein the first matrix array of sensor components are divided into a plurality of rows of first sensor components connected via a plurality of first connecting lines to the first signal lines and a plurality of columns of second sensor components connected via a plurality of second connecting lines to the second signal lines, each of the plurality of first connecting lines being non-overlapping with each of the plurality of second connecting lines;
a second planar substrate disposed opposite to the first planar substrate;
a plurality of third signal lines formed on the second planar substrate;
a plurality of fourth signal lines formed on the second planar substrate;
a second matrix array of sensor components formed on the second planar substrate,
wherein the second matrix array of sensor components are divided into a plurality of rows of third sensor components connected via a plurality of third connecting lines to the third signal lines and a plurality of columns of fourth sensor components connected via a plurality of fourth connecting lines to the fourth signal lines, each of the plurality of third connecting lines being non-overlapping with each of the plurality of fourth connecting lines,
wherein the second matrix array of sensor components faces the first matrix array of sensor components respectively, any one of the first sensor components and a corresponding one of the fourth sensor components construct a pressure sensor, any of the second sensor components and a corresponding one of the third sensor components construct a pressure sensor,
wherein the plurality of first signal lines is only disposed on a first portion of the first planar substrate, the plurality of second signal lines is only disposed on a second portion of the first planar substrate, each of the plurality of first signal lines is horizontal in direction, each of the plurality of second signal lines is vertical in direction, and each of the plurality of first signal lines is disconnected from each of the plurality of second signal lines,
wherein the plurality of third signal lines is only disposed on a first portion of the second planar substrate, the plurality of fourth signal lines is only disposed on a second portion of the second planar substrate, each of the plurality of third signal lines is horizontal in direction, each of the plurality of fourth signal lines is vertical in direction, and each of the plurality of third signal lines is disconnected from each of the plurality of fourth signal lines,
wherein each sensor component of the first matrix array comprises a first conductive loop formed on the first planar substrate; and
wherein each sensor component of the second matrix array comprises a second conductive loop formed on the second planar substrate.

2. The pressure-sensing device of claim 1, wherein each of the conductive loops of the sensor components is a hexagonal shape.

3. The pressure-sensing device of claim 1, wherein each sensor component of the first matrix array comprises:
a plurality of first conductive lines disposed within and connected to the first conductive loop, and arranged in a first direction.

4. The pressure-sensing device of claim 3, wherein each sensor component of the second matrix array comprises:
a plurality of second conductive lines disposed within and connected to the second conductive loop, and arranged in a second direction.

5. The pressure-sensing device of claim 1, wherein the sensor components of the first matrix array consist of conductive material printed on the first planar substrate, and the sensor components of the second matrix array consist of conductive material printed on the second planar substrate.

6. The pressure-sensing device of claim 1, wherein the pressure sensor pad further comprises:
a plurality of spacers disposed between the first planar substrate and the second planar substrate.

7. The pressure-sensing device of claim 6, wherein the spacers are divided into first spacers fastened on the first planar substrate and second spacers fastened on the second planar substrate, and the first spacers and the second spacers are coupled together, so as to prevent the first and second matrix arrays of the sensor components from misalignment.

8. The pressure-sensing device of claim 1, wherein the first planar substrate or the second planar substrate is flexible for allowing contact between the first and second planar substrates when a sufficient force is applied to the first or second planar substrates to cause the first or second planar substrates to contact the opposing substrate.

9. The pressure-sensing device of claim 1, wherein each of the sensor components is same in size.

10. The pressure-sensing device of claim 1, wherein each of the sensor components is same in shape.

11. The pressure-sensing device of claim 1, wherein each of the sensor components has a convex shape.

12. The pressure-sensing device of claim 1, wherein the first sensor components are formed on only one side of the first planar substrate, and the second sensor components are formed on only one side of the second planar substrate.

13. The pressure-sensing device of claim 1, wherein the first and third signal lines are select lines, and the second and fourth signal lines are read lines; alternatively, the first and third signal lines are read lines, and the second and fourth signal lines are select lines.

14. A pressure-sensing device comprising:
a pressure sensor pad comprising:
a planar substrate;
a plurality of first signal lines formed on the planar substrate;
a plurality of second signal lines formed on the planar substrate; and
a first matrix array of sensor components formed on the planar substrate,
wherein the first matrix array of sensor components are divided into a plurality of rows of first sensor components connected via a plurality of first connecting lines to the first signal lines and a plurality of columns of second sensor components connected via a plurality of second connecting lines to the second signal lines, each of the plurality of first connecting lines being non-overlapping with each of the plurality of second connecting lines,
wherein the plurality of first signal lines is only disposed on a first portion of the planar substrate, the plurality of second signal lines is only disposed on a second portion of the planar substrate, each of the plurality of first signal lines is horizontal in direction, each of the plurality of second signal lines is vertical in direction, and each of the plurality of first signal lines is disconnected from each of the plurality of second signal lines,
wherein the pressure sensor pad comprises a second planar substrate that is disposed opposite to the planar substrate,
wherein the second planar substrate comprises:
a plurality of third signal lines formed on the second planar substrate;
a plurality of fourth signal lines formed on the second planar substrate; and
a second matrix array of sensor components formed on the second planar substrate,
wherein the second matrix array of sensor components are divided into a plurality of rows of third sensor components connected via a plurality of third connecting lines to the third signal lines and a plurality of columns of fourth sensor components connected via a plurality of fourth connecting lines to the fourth signal lines,
wherein the plurality of third signal lines is only disposed on a first portion of the second planar substrate, the plurality of fourth signal lines is only disposed on a second portion of the second planar substrate, each of the plurality of third signal lines is horizontal in direction, each of the plurality of fourth signal lines is vertical in direction, and each of the plurality of third signal lines is disconnected from each of the plurality of fourth signal lines, each of the plurality of third connecting lines being non-overlapping with each of the plurality of fourth connecting lines,
wherein each sensor component of the first matrix array comprises a conductive loop formed on the first planar substrate,
wherein each sensor component of the second matrix array comprises a conductive loop formed on the second planar substrate, and
wherein the plurality of rows of first sensor components faces the plurality of columns of fourth sensor components respectively, and the plurality of columns of second sensor components faces the plurality of rows of third sensor components respectively.

15. The pressure-sensing device of claim 14, wherein a number of the first signal lines, a number of the rows of the first sensor components, a number of the rows of the second sensor components, a number of the third signal lines, a number of the rows of the third sensor components, and a number of the rows of the fourth sensor components are equal.

16. The pressure-sensing device of claim 14, wherein a number of the second signal lines, a number of the columns of the second sensor components, a number of the fourth signal lines, and a number of the columns of the fourth sensor components are equal.

17. The pressure-sensing device of claim 14, wherein a number of the columns of the first sensor components equals a number of the columns of the third sensor components.

18. The pressure-sensing device of claim 14, wherein:
a number of columns of the sensor components on the first matrix array is odd, and a number of the columns of the first sensor components and a number of the columns of the second sensor components differ by 1.

19. The pressure-sensing device of claim 18, wherein a number of columns of the sensor components on the second matrix array is odd, a number of the colunms of the third sensor components equals the number of the columns of the first sensor components, and a number of the columns of the fourth sensor components equals the number of the columns of the second sensor components.

20. The pressure-sensing device of claim 19, wherein a sensor constructed from a sensor component in the middle column of the first matrix array and a sensor component in the middle column of the second matrix array is read using either a first signal line and a third signal line or a second signal line and a fourth signal line.

* * * * *